US006650919B2

(12) United States Patent
Edelberg et al.

(10) Patent No.: US 6,650,919 B2
(45) Date of Patent: Nov. 18, 2003

(54) ENHANCED BIOLOGICALLY BASED CHRONOTROPIC BIOSENSING

(75) Inventors: Jay M. Edelberg, New York, NY (US); David J. Christini, Brooklyn, NY (US)

(73) Assignee: Cornell Research Foundation, Inc., Ithaca, NY (US)

(*) Notice: Subject to any disclaimer, the term of this patent is extended or adjusted under 35 U.S.C. 154(b) by 7 days.

(21) Appl. No.: 09/848,064

(22) Filed: May 3, 2001

(65) Prior Publication Data

US 2002/0062072 A1 May 23, 2002

Related U.S. Application Data

(60) Provisional application No. 60/201,465, filed on May 3, 2000.

(51) Int. Cl.$^7$ ................................................. A61B 5/05
(52) U.S. Cl. .................. 600/345; 600/300; 600/365; 600/373; 204/403.01; 435/176
(58) Field of Search ....................... 204/403.01–403.15; 436/63, 149, 806; 435/176; 422/82.01, 82.02; 600/345–361, 365, 372–381, 300

(56) References Cited

U.S. PATENT DOCUMENTS

| | | | | |
|---|---|---|---|---|
| 5,187,096 A | * | 2/1993 | Giaever et al. | 435/287.1 |
| 5,993,378 A | * | 11/1999 | Lemelson | 73/30.01 |
| 6,117,643 A | * | 9/2000 | Simpson et al. | 435/7.1 |
| 6,171,239 B1 | * | 1/2001 | Humphrey | 600/372 |
| 6,455,303 B1 | * | 9/2002 | Orwar et al. | 435/287.1 |

OTHER PUBLICATIONS

Aird, W., et al., (1997) "Vascular Bed–specific Expression of an Endothelial Cell Gene Is Programmed by the Tissue Microenvironment," *The Journal of Cell Biology* 138(5): 1117–1124.
Anderson, J.L., et al., (1998, Part II) "A Software Sensor Using Neural Networks for Detection of Patient Workload," *Pace* vol. 21: 2204–2298.
Anglade, F., et al., (1987) "A study of the action of clonidine on secretion from the adrenal medulla in dogs," *Br. J. Pharmac.* 91: 481–486.
Anversa, P., et al., (1989) "Morphometric analysis of coronary capillaries during physiologic myocardial growth and induced cardiac hypertrophy: A Review," *Int. J. Microcirc: Clin Exp* 8: 353–363.
Bousse, Luc, (1996) "Whole cell biosensors," *Sensors and Actuators B* 34: 270–275.
Boute, W., et al., (1988, Part II) "Introduction of an Automatic QT Interval Driven Rate Responsive Pacemaker," *Pace* vol. 11: 1804–1814.
Brignole, M., et al., (1990, Part II) "Pacing for Carotid Sinus Syndrome and Sick Sinus Syndrome," *Pace* vol. 13: 2071–2075.

Celiker, A., et al., (1998, Part I) "Comparison of Normal Sinus Rhythm and Pacing Rate in Children with Minute Ventilation Single Chamber Rate Adaptive Permanent Pacemakers," *Pace* vol. 21: 2100–2104.
Christini, D. J., et al., (2001) "Direct biologically based biosensing of dynamic physiological function," *Am. J. Physiol. Heart Circ. Physiol* 280: H2006–H2010.
Christini, D.J., et al., (1999) "Practical Real–Time Computing System for Biomedical Experiment Interface," *Annals of Biomedical Engineering*, vol. 27: 180–186.
Clémenty, J., et al., (1999) "Clinical Significance of Multiple Sensor Options: Rate Response Optimization, Sensor Blending, and Trending," *The American Journal of Cardiology*, vol. 83(5B): 166D–171D.
Clémenty, J., et al., (1998, Part II) "Dual Chamber Rate Responsive Pacing System Driven by Contractility," Final Assessment After 1–Year Follow–up. *Pace* vol. 21: 2192–2197.
Connelly, D.T., et al., (1993) "Initial Experience with a New Single Chamber, Dual Sensor Rate Responsive Pacemaker," *Pace* vol. 16: 1833–1841.
Cook, C.J., (1997) "Real–Time Measurements of Corticosteroids in Conscious Animals Using an Antibody–Based Electrode," *Nature Biotechnology*, vol. 15: 467–471.
Cornell, B.A., et al., (1997) "A Biosensor that Uses Ion–Channel Switches," *Nature*, vol. 580–583.
Den Heijer, P., et al., (1989) "Improved Rate Responsive Algorithm in QT Driven Pacemakers—Evaluation of Initial Response to Excercise," *Pace* vol. 12: 805–811.
Edelberg, J.M., et al., (1998) "Enhancement of Murine Cardiac Chronotropy by the Molecular Transfer of the Human $\beta_2$ Adrenergic Receptor cDNA," *J. Clin. Invest.*, vol. 101, No. 2: 337–343.

(List continued on next page.)

Primary Examiner—Robert L. Nasser
Assistant Examiner—Patricia C. Mallari
(74) Attorney, Agent, or Firm—Schwagman, Lundberg, Woessner & Kluth, P.A.

(57) ABSTRACT

The present invention provides implantable physiological or pathophysiological biosensors. The subject biosensors comprise tissue or cells capable of carrying out a physiological or pathophysiological function, which can be used to monitor a chemical, physiological or pathophysiological variable associated with the physiological or pathophysiological function. In one embodiment, the tissue or cells are coupled via an electrical interface to an electronic measuring device or an electronic amplifying device. In another embodiment, the tissue or cells are coupled via an electrical interface to endogenous tissue or cells, including the blood. Preferably, the tissue or cells are excitable tissue or cells such as cardiac tissue or cells and neuronal tissue or cells. The subject biosensors may be placed, inserted or implanted in any animal including but not limited to a mouse, rat, rabbit, pig, cat, dog, cattle, horse, sheep or human. The present invention also provides various methods which employ a biosensor of the present invention. Such methods include a method of monitoring physiological or pathophysiological function, a method of regulating output of a signal to a subject, and a method for controlling heart function.

58 Claims, 9 Drawing Sheets

OTHER PUBLICATIONS

Fritz, J., et al., (2000) "Translating Biomolecular Recognition into Nanomechanics," *Science*, vol. 288: 316–318.

Fulmer, R.I., et al., "Transplantation of Cardiac Tissue into the Mouse Ear," *Department of Anatomy, Baylor University College of Medicine*: 273–281.

Greco, E.M., et al., (2000) "How to Program Rate Responsive Pacemakers," *Pace* vol. 23: 165–173.

Lau, C.P., et al., (1990, Part I) "Pacemaker Mediated Tachycardias In Single Chamber Rate Responsive Pacing," *Pace* vol. 13: 1575–1579.

Leung, S.K., et al., (1998) "An Integrated Dual Sensor System Automatically Optimized by Target Rate Histogram," *Pace* vol. 21: 1559–1566.

Luo, L., et al., (1999) "Ion Channel Sensor," *Analytical Letters*, 32(7): 1271–1286.

Makino, S., et al., (1999) "Cardiomyocytes Can Be Generated From Marrow Stromal Cells In Vitro," *J. Clin. Invest.*, vol. 103, No. 5: 697–705.

Maltsev, V.A., (1993) "Embryonic Stem Cells Differentiate In Vitro Into Cardiomyocytes Representing Sinusnodal, Atrial and Ventricular Cell Types," *Mechanisms of Development* 44: 41–50.

Marshall, A., et al., (1998) "DNA Chips: An Array of Possibilities," *Nature Biotechnology*, vol. 16: 27–31.

Moura, P.J., et al., (1987, Part I) "Chronotropic Response of an Activity Detecting Pacemaker Compared with the Normal Sinus Node," *Pace* vol. 10: 78–86.

Mulchandani, P., et al., (1999) "Biosensor for Direct Determination of Organophosphate Nerve Agents. 1. Potentiometric Enzyme Electrode," *Biosensors & Bioelectronics* 14: 77–85.

Naessens, M., et al., (1998) "Whole–Cell Biosensor for Direct Determination of Solvent Vapours," *Biosensors & Bioelectronics*, vol. 13, No. 3–4: 341–346.

Ogawa, H., et al., (1991) "Heart Rate Responses to Automatic Drugs in Sick Sinus Syndrome—Correlation with Syncope and Electrophysiologic Data," *Japanese Circulation Journal*, vol. 55: 15–23.

Owicki, J.C., et al., (1992) "Biosensors Based on the Energy Metabolism of Living Cells: The Physical Chemistry and Cell Biology of Extracellular Acidification," *Biosensors & Bioelectronics* 7: 255–272.

Pancrazio, J.J., et al., (1999) "Development and Application of Cell–Based Biosensors," *Annals of Biomedical Engineering*, vol. 27: 697–711.

Rendell, M.S., et al., (1998) "The Relationship of Laser—Doppler Skin Blood Flow Measurements to the Cutaneous Microvascular Anatomy," *Microvascular Research* 55: 3–13.

Rivard, A., et al., (1999) "Age–Dependent Impairment of Angiogenesis," *Circulation* 99(1): 111–120.

Rodriguez, R.D., et al., (1990) "Update on Sick Sinus Syndrome, a Cardiac Disorder of Aging," *Geriatrics*, vol. 45, No. 1: 26–36.

Rowe–Taitt, C.A., et al., (2000) "Array Biosensor for Detection of Biohazards," *Biosensors & Bioelectronics* 14: 785–794.

Strobel, J.S., et al., (2000) "Programming of Sensor Driven Pacemakers," *MD Consult—Journal Article*, vol. 18, No. 1: 1–22.

Sugiura, T., et al., (1998) "A Self–Tuning Effect of Membership Functions in a Fuzzy–Logic–Based Cardiac Pacing System," *Journal of Medical Engineering & Technology*, vol. 22, No. 3: 137–143.

Sutton, R., et al., (1986, Part II) "The Natural History of Sick Sinus Syndrome," *Pace* vol. 9: 1110–1114.

Updike, S.J., et al., (2000) "A Subcutaneous Glucose Sensor With Improved Longevity, Dynamic Range, and Stability of Calibration," *Diabetes Care*, vol. 23, No. 2: 208–214.

Wang, T.L., et al., (1994) "Sick Sinus Syndrome as the Early Manifestation of Cardiac Hemochromatosis," *Journal of Electrocardiology*, vol. 27, No. 1: 91–96.

Windecker, S., et al., (1998) "Two–Year Experience with Rate–Modulated Pacing Controlled by Mixed Venous Oxygen Saturation," *Pace* vol. 21: 1396–1404.

Wong, K.K., (1993) "Vascular Effects of Low and High Doses of Clonidine in Rats," *Artery* 20(4): 180–188.

\* cited by examiner

ENHANCED BIOLOGICALLY BASED CHRONOTROPIC BIOSENSING

This application claims priority from U.S. Provisional Application Ser. No. 60/201,465, filed May 3, 2000, which is hereby incorporated by reference.

This invention was made with government support under National Institutes of Health, Grant No. PO 1 HL593 12. The Government may have certain rights in the invention.

BACKGROUND OF THE INVENTION

Cardiac chronotropic incompetence is associated with increased morbidity and mortality (1-3). The majority of cases of symptomatic chronotropic incompetence are treated by implantation of a permanent electronic pacemaker.

Pacemaker responsiveness is one of the most recent developments in pacemaking technology. Designed to allow the pacemaker to meet the physiologic needs of the individual, pacemaker response elements are most clinically applicable in cases of chronotropic incompetence. Responsive elements are biosensors of physiologic demand, commonly measuring $O_2$, temperature or movement as surrogates of input signals which direct endogenous cardiac chronotropic activity. Unfortunately, while the development of pacemaker responsiveness has improved the exercise tolerance of patients as compared to treatments with pacemakers without responsive elements (4), the potential of this approach has not yet been fulfilled (5, 6). Previous studies have demonstrated that when directly compared to the endogenous sinus nodal activity, pacemaker responsive elements may have only a 70% correlation with endogenous activity (7, 8). Moreover, inappropriate chronotropic responsiveness can contribute to diminished exercise tolerance and fatigue, and less commonly but more importantly, such dysregulation may lead to inappropriate tachycardias (9).

Advances in pacemaker responsiveness have focused both on improving the integration of the acquired sensory data and on employing the endogenous myocardium into the biosensory circuits. Studies have demonstrated that sophisticated programming with intensive complex or individualized programming may facilitate the blending of multiple sensory inputs in order to improve individual chronotropic regulation to enhance exercise performance (10-12). An alternative approach in chronotropic responsiveness research has been to attempt to exploit the chronotropic regulatory capacity of the endogenous cardiac myocardium. Pacemaking biosensors are being tested and developed to incorporate direct cardiac myocardial signals into the regulation of pacemaking including inputs of cardiac contractility (13), and QT intervals (14–16). Recently, neural network computer programs have been developed based on the morphology of intracardiac electrograms in an attempt to 'learn' physiologic sensing (17). While the integration of direct cardiac inputs may have advantages over the more common measurements of surrogate markers of physiologic demand, this approach relies on the sensing of pathologic tissue: the chronotropically incompetent heart. Indeed, the diversity of the primary or secondary disease processes underlying chronotropic incompetence often affects other components of the cardiac conduction system (18, 19), as well as myocardium (3). Hence, this associated pathology may significantly impair the ability of the endogenous heart to function as an accurate biosensor and transducer element for the prediction of heart rate.

Dynamic regulation of biological systems requires real-time assessment of relevant physiological needs. Biosensors, which transduce biological actions or reactions into signals amenable to processing, are well-suited for such monitoring. Typically, in vivo biosensors approximate physiological function via the measurement of surrogate signals. Biosensors derive utility from their inherent selectivity to specific biological signals and their physiologically relevant reactions [20]. Most biosensors are molecularly based, relying on a specific interaction between biomolecules such as antibodies [22, 22], enzymes [23, 24], ion channels [25, 26], or nucleic acids [20, 27, 28] and a target compound. Alternatively, cell-and tissue-based biosensors [29–31] offer inherent insight into physiological function by exploiting the selectivity of the receptors, channels, and enzymes that are part of the cell's functional structure. Most cell-and tissue-based biosensors are used for chemical detection—a task for which they are quite adept, but not one for which they specifically evolved.

The present invention employs the inherent biosensing capacity of excitable tissue in a healthy state. The present invention thus provides biologically-based biosensors for the direct measurement of physiological activity via functional integration of relevant governing inputs. The subject biosensors may be used to monitor physiological function and even replace or augment degraded sensing function of endogenous tissue. When implanted, the subject biosensors may be used as real-time, integrated bioprocessors of the complex inputs regulating dynamic physiological variables. The biosensors of the present invention provide biologically-tuned quantification of remote physiological function, and are therefore useful as exogenous electropotential interfaces for external or implantable devices.

SUMMARY OF THE INVENTION

The present invention provides implantable physiological or pathophysiological biosensors. The subject biosensors comprise tissue or cells capable of carrying out a physiological or pathophysiological function, which can be used to monitor a chemical, physiological or pathophysiological variable associated with the physiological or pathophysiological function. In one embodiment, the tissue or cells are coupled via an electrical interface to an electronic measuring device or an electronic amplifying device. In another embodiment, the tissue or cells are coupled via an electrical interface to endogenous tissue or cells, including the blood. Preferably, the tissue or cells are excitable tissue or cells. Examples of excitable tissue or cells include cardiac tissue or cells and neuronal tissue or cells.

The tissue or cells of a subject biosensor may be molecularly, genetically, or cellularly engineered. A physiological or pathophysiological variable monitored by the biosensor of the present invention may include, for example, heart rate regulation or heart rate dynamics. Another chemical, physiological or pathophysiological variable which may be monitored by a biosensor of the present invention is a level of a compound. Examples of such compounds include but are not limited to blood glucose, insulin, thyroid hormone, clotting factors and components, endocrine hormone, paracrine hormone, autocrine hormone, antibodies, receptor antagonists, ligands, antigens, antagonists, signal pathway cofactors, signal pathway components, pathogens, drugs, metabolites and toxins.

In accordance with the present invention, a subject biosensor may be implanted or inserted in an animal. Preferably, the animal is a mammal. Examples of mammals into which a subject biosensor may be implanted include but are not limited to a mouse, rat, rabbit, pig, cat, dog, cattle, horse or sheep. Most preferably, the mammal is human.

The present invention also provides a method for monitoring physiological or pathophysiological function. The method comprises placing into a subject, tissue or cells capable of carrying out a physiological or pathophysiological function within the subject, which tissue or cells can be used to monitor a chemical, physiological or pathophysiological variable associated with the physiological or pathophysiological function of the subject. The exogenous tissue or cells are then monitored for physiological or pathophysiological function. Preferably, tissue or cells for use in the method comprise excitable tissue or cells. Examples of excitable tissue or cells for use in the method include cardiac tissue or cells, and neuronal tissue or cells.

In the method for monitoring a physiological or pathophysiological function, the tissue or cells used for placement into a subject may be coupled via an electrical interface to an electronic measuring device. The tissue or cells may also be coupled via an electrical interface to endogenous tissue or cells. Examples of physiological or pathophysiological variables which may be measured according to the method include heart rate regulation or heart rate. Also in accordance with the method, a chemical, physiological or pathophysiological variable may be a level of a compound such as e.g., blood glucose, insulin, thyroid hormone, clotting factors and components, endocrine hormone, paracrine hormone, autocrine hormone, antibodies, receptor antagonists, ligands, antigens, antagonists, signal pathway cofactors, signal pathway components, pathogens, drugs, metabolites, and toxins.

In the method for monitoring a physiological or pathophysiological function, the tissue or cells may be implanted in an animal. The tissue or cells may also be incorporated into a device that is placed inside an animal. The method may be performed on any animal such as, for example, a mammal. Preferred mammals for use in the method include a mouse, rat, rabbit, pig, cat, dog, cattle, horse and sheep. Preferably, the mammal is a human.

The present invention further provides a method of regulating output of a signal, substance, or action to a subject. The method comprises placing within the subject, exogenous tissue or cells capable of carrying out a physiological or pathophysiological function, which tissue or cells can be used to monitor a chemical, physiological or pathophysiological variable associated with the physiological or pathophysiological function. The exogenous tissue or cells are coupled to an interventional device or a delivery device, and the output of a signal, substance, or action from the interventional or delivery device in response to the physiological or pathophysiological function of the exogenous tissue or cells, is regulated.

In response to the electrical or chemical signal, the delivery device delivers an electrical or mechanical stimuli. Alternatively, the delivery device delivers a drug or a compound. Preferably, the tissue or cells are excitable tissue or cells. Examples of excitable tissue or cells include cardiac tissue or cells and neuronal tissue or cells. A physiological or pathophysiological variable monitored may be e.g., heart rate regulation or heart rate dynamics. A chemical, physiological or pathophysiological variable may be e.g., a level of a compound such as blood glucose, insulin, thyroid hormone, clotting factors and components, endocrine hormone, paracrine hormone, autocrine hormone, antibody, receptor antagonists, ligands, antagonists, antigens, signal pathway cofactors, and signal pathway components, pathogens, drugs, metabolites, or toxins.

In accordance with a method of regulating the output of a signal to a subject, the exogenous tissue or cells may be implanted in a mammal. In an alternative embodiment, the tissue or cells may be incorporated into a device that is placed inside a mammal. The mammal may be selected from the group consisting of a mouse, rat, rabbit, pig, cat, dog, horse, cattle and a sheep. Preferably, the mammal is a human.

In still another aspect of the invention, there is provided a system for controlling heart function. The system comprises exogenous tissue or cells, capable of carrying out a physiological or pathophysiological function, placed within a subject; and an electrical connection placed between the exogenous tissue or cells and the natural pacemaker region of the heart. Preferably, excitable tissue or cells are used such as e.g., cardiac tissue or cells, or neuronal tissue or cells. If desired, an amplifier may be added to the system in order to boost the signal from the exogenous tissue or cells. In another embodiment of the system, the exogenous tissue or cells are connected to an electronic pacemaker. The exogenous tissue or cells may comprise cells that are molecularly, genetically, or cellularly engineered. A subject which may utilize the system for controlling heart function may be any animal. Preferably, the animal is a mammal. Examples of mammals which may utilize the system include but are not limited to a mouse, rat, rabbit, pig, cat, dog, cattle, horse or sheep. Most preferably, the mammal is human.

BRIEF DESCRIPTION OF THE DRAWINGS

FIG. 2d shows the first derivative versus time $d\hat{R}R(t)/dt$ for the polynomial fits of the endogenous (open triangles) and second exogenous heart (shaded circles). When time-shifted to account for the exogenous phase lag (i.e., the 72s mean delay between the endogenous and exogenous derivative zeros), the two derivatives had the same sign for 79% of the record. 13/15 trials had concordance>70% (mean 85±11%). Such high concordance quantitatively confirms that the exogenous heart effectively tracked increases and decreases in endogenous heart rate.

In FIG. 1a, the correlation coefficient r=0.94 indicates that there is a strong one-to-one linear relationship (with slope m=3.33 ms/ms) between the exogenous and endogenous RR. 5/13 positive trials had r>0.70 ($\bar{r}$=0.85±0.10, m=2.40±1.15 ms/ms). 4 of the remaining 8 positive trials had at least one distinct segment (of at least 500 consecutive s) of effective absolute sensing, with r>0.85 (r=0.91±0.04, $\bar{m}$=2.06±1.12 ms/ms for segments of at least 500s). One such trial (the same exogenous heart trial as that of FIG. 2c) is shown in FIG. 3b.

FIG. 4a represents one trial where 100 μg of propranolol was delivered via IP injection at t=121s. The inset shows a magnified portion of the endogenous data. Shortly after injection, endogenous and exogenous rates slowed (stage B) relative to baseline (stage A) in 4 out of 5 trials (aggregate values, as defined in Methods, are shown in FIG. 4c). The exogenous slowing is evidence of autonomic and/or humoral control. In the trial shown in FIG. 4b (same mouse as in FIG. 4a, but performed on a different day), 2.0 mg clonidine was delivered via IP injection at t=49s. Shortly after injection, the endogenous rate slowed rapidly (stage B') in 6 out of 7 trials. In contrast, the exogenous rate continued its preinjection trend. After stage B', both the endogenous and exogenous hearts slowed. In all six trials, the endogenous hearts slowed considerably more during stage B' than stage B, while the exogenous hearts slowed more during stage B than stage B'.

FIG. 8a shows a representative example of mean RR intervals versus time for the endogenous heart. FIG. 8b shows a representative example of mean RR intervals versus time for the ES-cardiac myocyte transplant of a mouse pretreated with PDGF. FIG. 8c depicts first order derivatives versus time dRR/dt of the polynomial fits of the RR dynamics (c), and demonstrated an 80% concordance in sign for the trial.

DETAILED DESCRIPTION OF THE INVENTION

Figure 1:
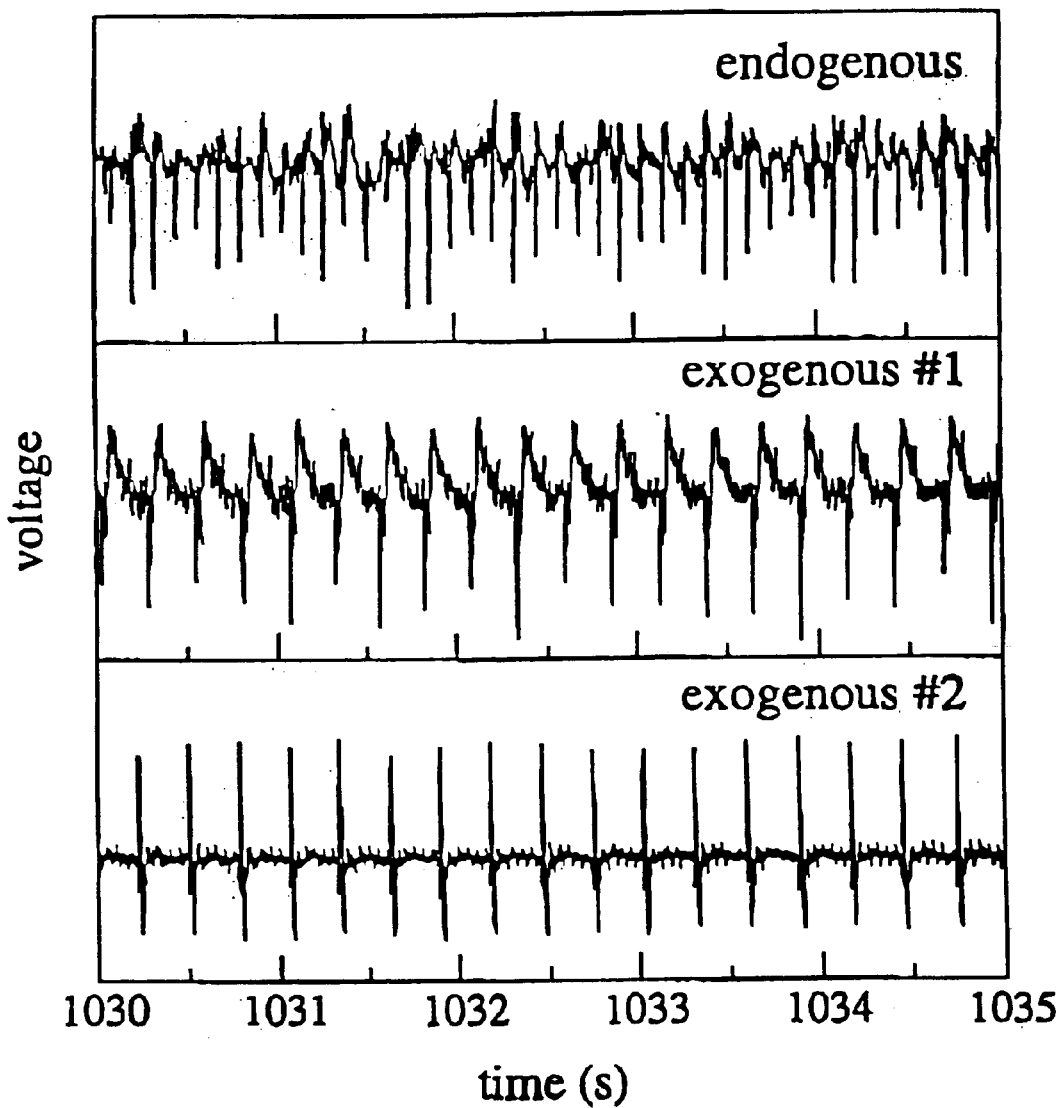
FIG. 1 shows the simultaneous electrical activity of the endogenous heart and bilateral exogenous hearts in a representative trial. Shown are voltage versus time tracings for the endogenous heart (top panel) and two exogenous hearts (exogenous heart #1 and #2)) of an adult mouse 17 days after bilateral pinnal heart transplantation. The three hearts beat at unique, but not unrelated rates, with the exogenous hearts beating at rates approximately half that of the endogenous heart.

In accordance with the present invention, it has been surprisingly discovered that implantation of chronotropically-competent cardiac allografts or stem cell-derived cardiac myocytes, distant from and not directly linked to the endogenous heart, result in the exogenous tissue serving as an effective relative endogenous rate sensor. The resultant biologically-tuned quantification of remote physiological function is the basis for using excitable tissue as a biosensor which can serve as an exogenous electropotential interface for external or implantable devices.

Thus, the present invention provides implantable physiological or pathophysiological biosensors. A biosensor of the present invention is made of tissue or cells capable of carrying out a normal physiological or pathophysiological function associated with that tissue. In a preferred embodiment, the tissue or cells which make up a subject biosensor are excitable tissue or cells. Excitable tissues respond to parameters or signals within the body and allow the integration or transmission of these signals as a feature of their excitable properties. The function carried out by the excitable tissue or cells can then be used to monitor the parameters affecting the function. Preferred tissues or cells for use in the biosensors of the present invention are cardiac tissue or cells or neuronal tissue or cells. As used herein, the term "monitor" can mean one or more of the following: to measure, detect, keep track of, scrutinize, check, and/or test.

For example, cardiac tissue normally beats in response to various signals within the body. The physiological function of cardiac cells can then be used to monitor and/or respond to one or more physiological or pathophysiological variables associated with the physiological or pathophysiological function. Other excitable tissues may be used to monitor and/or respond to physiological or pathophysiological events. Intestinal tissue, for example, contracts in response to various physiological and pathophysiological events. Neuronal cells have developed highly complex electropotential activities in response to signals in the body.

The biosensors of the present invention have particular use in cardiac chronotropy applications because the humoral signals sensed by the exogenous tissue of a subject biosensor are still present when an endogenous heart is chronotropically impaired. The biosensors of the present invention with their direct biologically-timed approach thus offer advantages over current electronic pacemaker sensing of minute ventilation, oxygen pressure/saturation, and other surrogate signals of physiologic demand to estimate optimal beat rate.

Cardiac tissue or cells and neuronal tissue or cells may be obtained from various sources such as donated organs or live donors. Heart tissue or cells and neuronal tissue or cells from either a donated organ or a live donor may be further cultured prior to their use in a subject biosensor. Methods for culturing cardiac tissue or cells are well known and can be found in e.g., Rust, Westfall & Metzger *Mol Cell Biochem.* 1998 Apr;181(1–2):143–55, which is incorporated by reference herein as if fully set forth. Methods for culturing neuronal tissue or cells are also well known and may be found in e.g., Barnea & Roberts, *Brain Res Protoc.* 1999 Jul;4(2): 156–64, which is also incorporated by reference herein as if fully set forth. The organ donor and biosensor recipient should be as closely phylogenetically related as possible. For example, when a subject biosensor is to be implanted in an animal, animal cardiac tissue or cells and/or neuronal tissue or cells may be used. When the biosensor recipient is a human, cardiac tissue or cells and/or neuronal tissue or cells from a pig may be used. Preferably, human tissue or cells are used in a biosensor to be implanted in a human.

The biosensor recipient may serve as tissue or cell donor. Alternatively, cardiac tissue or cells, or neuronal tissue or cells from a donor other than the biosensor recipient may be used. When cardiac or neuronal tissue or cells from a donor other than the biosensor recipient is used, the tissue or cells and the individual recipient are HLA typed and matched.

The amount of tissue or cells which are used in a subject biosensor may vary depending on the height, weight, gender, age and condition of the recipient. Generally speaking, when a donor heart is used, an excised portion of about 1–2 mm$^3$ may be used. Any tissue of the heart may be employed, such as e.g., sinusnodal tissue. When neuronal or cardiac cells are obtained through culturing, as little as one cell to about $10^7$–$10^8$ cells may be used.

The tissue or cells which make up a subject biosensor may be stem cell-derived cardiac myocytes. In this embodiment, stem cells are used to culture cardiac myocytes. Stem cells may be obtained from various sources such as e.g., bone marrow, peripheral blood, organs, or tissue, including fat or umbilical cord blood, as well as any combination of these sources. The stem cells may be allogeneic (foreign to a biosensor recipient) or syngeneic (same to the biosensor recipient). Preferably, the biosensor recipient provides a syngeneic source of stem cells for culturing cardiac myocytes.

The tissue or cells of the invention may be molecularly, genetically, or cellularly engineered to expand the range of monitored parameters and the utility of a subject biosensor. By "molecularly engineered" it is meant that the excitable tissue or cells are treated with a compound which is heterologous or foreign to the cell to alter or direct activity. For example, the tissue or cells may be treated with a compound which alters the behavior of the tissue or cells. Examples of such compounds include but are not limited to those falling under the categories of cytokines, growth factors or hormones. The cells or tissue may be treated either in vitro, in vivo, or ex vivo.

By "genetically engineered," it is meant that the tissue or cells are transgenic, i.e., the tissue or cells comprise coding sequence for a protein which is heterologous or foreign to the genome of the cell. Alternatively, by "genetically engineered," it is meant that the tissue or cells express a gene product which is not normally expressed in the tissue or cells or else the tissue or cells over-express the gene product. Thus, for example, by genetically engineering one or more cells to express a cell surface receptor or ligand, signaling component, transcription factor or cofactor, such genetically engineered cells when placed in a subject are useful for monitoring physiologic or pathophysiologic signals in the subject.

Methods for genetically engineering cardiac myocytes or neuronal cells are known and are described in Edelberg, J. M., Aird, W. C. & Rosenberg, R. D., "Enhancement of murine cardiac clironotropy by the molecular transfer of the human beta2 adrenergic receptor CDNA" *J Clin Invest* 101, 337–343 (1998) and Lin H, Parmacek MS, Morle G, et al. "Expression of recombinant genes in myocardium in vivo after direct injection of DNA" *Circulation* 1990;82:2217–21, which are incorporated by reference herein as if fully set forth.

By "cellularly engineered," it is meant that the cellular composition, growth architecture, geometry or intracellular connections are modified as to direct or alter activity. For example, the cells may be grown in different conformations such as in a circular arrangement or in an aggregate. Such different conformations may be achieved by well known methods in the art such as physical agitation of cells in culture or e.g., growing cells on silicon chips or other biocompatible surfaces having surface etchings or treatments which direct the growth of cells in different directions.

A biosensor of the present invention may be placed in the body where it can communicate with monitoring devices either outside the body (external) or also within the body (internal). Such devices may be coupled to recording devices as well as to devices which deliver therapies such as drugs, electrical stimulations, or other agents or actions.

Thus the tissue or cells which make up a biosensor of the present invention may consist of cells which have been engineered to produce different proteins such as e.g., coagulation factors, serotonin, growth factors, hormones, or any desirable receptor. Examples of growth factors include but are not limited to platelet-derived growth factor (PDGF) or vascular endothelial growth factor (VEGF). Examples of receptors for which the tissue or cells may be engineered to produce include but are not limited to G protein coupled receptors (GPCR) for measurement of proteases such as thrombin, and trypsin. Cells may also be engineered to produce signal proteins such as dopamine or serotonin or non-GPCRs such as tyrosine kinase receptors. The nucleic acid sequences coding for the aforementioned proteins are widely known and available.

The exogenous tissue or cells which make of a subject biosensor may be coupled via an electrical interface to an electronic measuring device or an electronic amplifying device. This embodiment is especially useful for use in monitoring physiological or pathophysiological function. For example, a subject biosensor comprising exogenous tissue or cells coupled via an electrical interface to an electronic measuring device or an electronic amplifying device is especially useful in the clinical setting of sick sinus syndrome. Examples of electrical interfaces include but are not limited to silicon chips, magnetic field sensors, and field electrodes. Examples of electronic measuring devices include electrodes and field effect transistors. Examples of electronic amplifying devices include operational amplifier circuits. An example of an electrical interface includes oxidized silicon.

Alternatively, the exogenous tissue or cells which may be coupled directly to endogenous tissue or cells. For example, exogenous cardiac tissue or cells may be placed within a subject and an electrical connection placed between the exogenous tissue or cells and the natural pacemaker region of the heart. This embodiment is especially useful in the clinical setting of improving pacemaker responsiveness in patients exhibiting symptomatic chronotropic incompetence.

Numerous chemical, physiological or pathophysiological variables may be monitored by the biosensors of the present invention. Such variables include for example, heart rate regulation or heart rate dynamics. Chemical, physiological or pathophysiological variables such as the level or activity of a compound or cellular action may also be monitored. Examples include the level or activity of blood glucose, insulin, thyroid hormone, clotting factors and components, endocrine hormone, paracrine hormone, autocrine hormone, antibody, fibrin formation, platelet aggregation, receptor antagonists, ligands, antagonists, signal pathway cofactors, signal pathway components, pathogens, drugs, metabolites, and toxins. The wide array of chemical, physiological and pathophysiological variables which may be monitored by the biosensors of the present invention indicate that the biosensors may be used to monitor, respond to, and intervene in, pathways and functions involving many different organs and organ systems.

A biosensor of the invention may be placed into a recipient subject, either implanted directly or as part of a device. As used herein, the terms "implant," "implantation," "place," "placement, " or "insert," as well as variations thereof, may be used interchangeably. "Implantation" may, in some instances, connote more permanence than "placement." Thus, a subject biosensor may be inserted in an animal recipient by means of a catheter or tubing comprising cells or tissues or through a surgical procedure. If the biosensor is to remain in an animal recipient long term, the placement may also be referred to as implantation.

The nature of a device which may form part of a biosensor of the present invention can vary. For example, tissue or cells may be placed on the tips of a catheter, tube or tubing which is then placed into an animal recipient. The device may also be a wire which is coated with tissue or cells and then put in contact with blood, such as when placed within an artery or vein. Preferably, the tissue or cells are excitable tissue or cells. In this aspect of the invention, the wire serves as a signaling device in detecting the level of a physiological or pathophysiological variable. The wire may serve as a signaling device upon detection of a level or activity of a compound such as e.g., blood glucose, insulin, thyroid hormone, clotting factors and components, endocrine hormone, paracrine hormone, autocrine hormone, antibodies, receptor antagonists, ligands, antigens, antagonists, signal pathway cofactors, signal pathway components, pathogens, drugs, metabolites, and toxins. For example, a recipient patient may be monitored for clotting factors in order to determine the level of blood thinning. A patient may also be monitored for fibrin formation or platelet aggregation. The wire may be further connected to a another device. For example, a wire having cells or tissues placed thereon may be used to monitor glucose level. The wire may be further connected to an insulin pump which pump may be placed externally or internally. As another example, the wire may serve to signal the growth of a tumor. Another example of a device which may form part of a subject biosensor are wire leads connected to a recipient heart, either through direct implantation of the biosensor in the recipient heart tissue or vasculature or indirectly through the placement of the wires of the biosensor device in the recipient heart tissue or vasculature. In still another example, the device may be an electronic pacemaker having a component which connects to the body. The component may house exogenous tissue or cells.

A biosensor recipient may be any animal. Preferably, the animal is a mammal. Examples of mammals which may be recipients of a subject biosensor include but are not limited to a mouse, rat, rabbit, pig, cat, dog, cattle, horse or sheep. Preferably, the mammal is a human.

The present invention also provides a method for monitoring a physiological or pathophysiological function. Tissue or cells capable of carrying out a physiological or pathophysiological function, which can be used to monitor a chemical, physiological or pathophysiological variable associated with the physiological or pathophysiological function are placed into a mammal, either implanted directly or as part of a device. The physiological or pathophysiological function of the exogenous tissue or cells is then monitored.

The invention may also be used to regulate the output of a signal, substance, or action from an interventional device or a delivery device. In this aspect of the invention, the monitoring function of the exogenous tissue or cells is integrated with an interventional device or delivery device to regulate the delivery of a signal, substance, or action to a subject. Examples of signals include electrical or chemical signals. An electrical signal includes e.g., a pacemaker signal. A chemical signal might be e.g., a drug. Examples of substances may be a hormone such as insulin, factors such as a growth factor, a polymer such as heparin, and may also include a drug. An example of an action is a mechanical action or cell or tissue depolarization.

As described above, numerous chemical, physiological or pathophysiological variables may be monitored by the biosensors of the present invention. In addition to heart rate regulation or heart rate dynamics, chemical, physiological or pathophysiological variables such as the level or activity of a compound or cellular action may be monitored. Examples include the level or activity of blood glucose, insulin, thyroid hormone, clotting factors and components, endocrine hormone, paracrine hormone, autocrine hormone, antibody, fibrin formation, platelet aggregation, receptor antagonists, ligands, antagonists, signal pathway cofactors, signal pathway components, pathogens, drugs, metabolites, and toxins.

As described above, the wide array of chemical, physiological and pathophysiological variables which may be monitored by the biosensors of the present invention indicate that the biosensors may be used to monitor, respond to, and intervene in, pathways and functions of many different organs and organ systems. Regulating the output of a signal, substance, or action in a subject may therefore be used to intervene in pathways and functions of many different organs and organ systems.

As described above, exogenous tissue or cells capable of carrying out a physiological or pathophysiological function, which can be used to monitor a chemical, physiological or pathophysiological variable associated with the physiological or pathophysiological function, are placed into the subject, either implanted directly or as part of a device as hereinbefore described. The exogenous tissue or cells are connected to a interventional or delivery device. The output of a signal, substance, or action from the interventional device or delivery device is then regulated in response to the physiological or pathophysiological function of the exogenous tissue or cells.

Examples of delivery devices include but are not limited to an electronic pacemaker, insulin pump, or drug pump. Examples of interventional devices include but are not limited to alarm systems and mechanical devices. Such a mechanical mechanism may directly pump blood or contract the heart or other part of the vasculature to direct blood flow. Similarly a device may directly augment air exchange in the lungs.

The present invention further provides a system for controlling heart function. The system comprises exogenous tissue or cells and an electrical connection between the exogenous tissue or cells and the natural pacemaker region of the heart. The exogenous tissue or cells are capable of carrying out a physiological or pathophysiological function and may be used to monitor a chemical, physiological or pathophysiological variable associated with the physiological or pathophysiological function. In a preferred embodiment, the exogenous tissue or cells are excitable tissue or cells such as e.g., cardiac or neuronal tissue or cells. In a most preferred embodiment, the exogenous tissue or cells are cardiac tissue or cells. The electrical connection may include additional components such as an amplifier, a signal processor, or even a full electronic pacemaker which responds to the output from the tissue or cells.

The biosensors or the present invention may be placed, inserted or implanted in various locations within an animal subject. For example, a subject biosensor may be placed in a subcutaneous pocket anywhere on the body. Other locations for implantation of a subject biosensor include for example, the vascular lumen. The heart of a biosensor recipient may also be the location for a biosensor of the present invention. Such a location is especially preferred when the biosensor is used for controlling heart function.

Implantation of a subject biosensor may be performed on an animal patient via a surgical procedure. Preferably, the patient is placed under a general or local anesthesia during the implantation procedure. The biosensor when implanted alone or as part of a device is preferably implanted in a manner such that the exogenous tissue or cells is in direct communication with blood-borne substances delivered via the endogenous blood supply. In addition, the biosensor may be directed to detect signals from the endogenous nervous system and as such would be preferably implanted in a manner such that the exogenous tissue or cells is in direct communication with neuronal signals delivered via the endogenous nervous system.

The following examples further illustrate the invention.

EXAMPLE I

Excitable tissue-based biosensors were developed by the implantation of chronotropically-competent cardiac allografts distant from (and not directly linked to) the endogenous heart. Neonatal FVB murine hearts were transplanted into the pinneas of three-month old FVB mice as previously described [32, 33]. Fifteen mouse hearts were implanted into nine mice (six mice received a transplanted heart in each ear, while three mice received a transplanted heart in only one ear).

Cardiac electrophysiological temporal dynamics were then monitored. Between 17 and 41 days post-transplantation, electrocardiographic (ECG) activity of the endogenous and exogenous hearts was measured following intraperitoneal (IP) anesthetization with avertin 2.5% (vol/vol). ECGs were acquired for an average of 45 min. (range: 27 to 117 min.) via an A-M Systems Model 1700 four-channel differential AC amplifier. Signals were bandpass filtered between 3.0 and 100.0 Hz, notch-filtered at 60.0 Hz, amplified 1000X, and sampled at 500 Hz by a National Instruments AT-MIO-1 6E-10 data acquisition board on a 266 MHz Intel Pentium-II computer running Real-Time Linux [30]. FIG. 1 shows simultaneous electrical activity of the endogenous heart and bilateral exogenous hearts in a representative trial. The three hearts beat at unique, but not unrelated (as seen in FIG. 2), rates, with exogenous rates approximately half of the endogenous rate.

Figure 2:
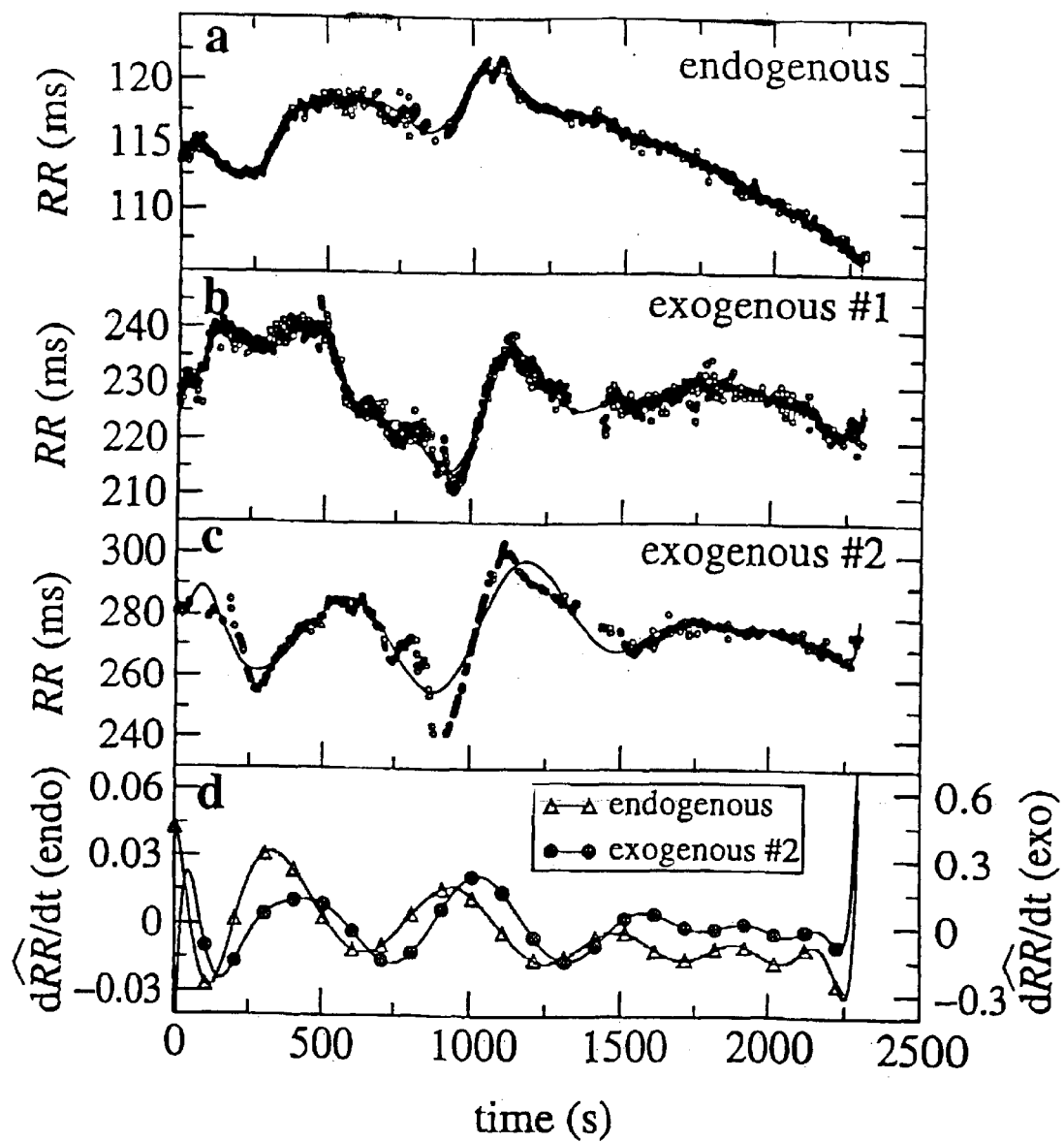
FIGS. 2a-2d show cardiac myocyte-based relative chronotropic biosensing activity measured by electrocardiographs. Shown are mean RR intervals RR versus time for the endogenous heart (FIG. 2a) and two exogenous hearts (FIGS. 2b and 2c) of an adult mouse 17 days after bilateral pinnal heart transplantations. The solid curve in each graph is $\hat{R}R(t)$, the best polynomial curve fit to the data. Occasionally, poor signal quality or high noise made R-wave annotation impossible, resulting in gaps in the corresponding graph. The RR-interval dynamics of both exogenous hearts effectively tracked those of the endogenous heart; i.e., there was a clear relationship between the rate trends (i.e., increasing/decreasing) of the three hearts.

Mean interbeat interval time series RR illuminated a clear relationship between exogenous and endogenous dynamics (FIG. 2). Post-acquisition automatic (with manual correction as needed) ECG R-wave annotation was performed using custom Linux C++software. Mean RR intervals $\overline{RR}$ were computed every two seconds so dynamics of the endogenous and exogenous signals, which have different inherent rates, could be compared quantitatively at synchronized time slices. (Two seconds was selected arbitrarily; no qualitative differences were found for interval lengths of one, five, or ten seconds.) The 15-trial endogenous mean $\overline{RR}_{max}-\overline{RR}_{min}=$ 31.2±24.9 ms while the exogenous mean $\overline{RR}_{max}-\overline{RR}_{min}=$ 100.8±72.0 ms.

The ability of the exogenous tissue to track relative temporal endogenous dynamics (i.e., increasing/decreasing trends) was quantified via analysis of the derivatives of polynomial curves fit to the $\overline{RR}$ time series (FIG. 2d). Each discrete $\overline{RR}$ Time series was fit (using Matlab 5.3. 1) to a continuous-time order P polynomial function given by $RR(t)=a_0 t^P + a_1 t^{P-1} + \ldots + a_{P-1} t + a_P$. P was selected as that order ($P \leq 25$) for which: (i) RR(t), when evaluated at the same discrete-time slices as $\overline{RR}$, accounted for at least 95% of the raw variability of $\overline{RR}$ (if this was not satisfied for any P<25, P was set to 25), and (ii) the exogenous and endogenous dRR(t)/dt functions, computed analytically over the time course of the record, had the highest concordance (i.e., the highest fraction of time that the two derivatives had the same sign), which is a measure of the ability of the exogenous heart to track the increases and decreases in endogenous rate.

TABLE 1

| Mouse # | Exogenous Heart # | Days since Transplant | $D\hat{R}R(t)/dt$ concordance | R |
|---|---|---|---|---|
| 1 | 1 | 41 | 0.69 | 0.60 |
| 2 | 1 | 41 | 1.00 | 0.94 |
| 3 | 1 | 41 | 0.90 | 0.82 |
| 4 | 1 | 17 | 1.00 | 0.86 |
| 4 | 2 | 17 | 0.47 | −0.62 |
| 5 | 1 | 17 | 0.79 | 0.70 |
| 5 | 2 | 17 | 0.51 | −0.64 |
| 6 | 1 | 17 | 0.77 | 0.03 |
| 6 | 2 | 17 | 0.79 | 0.42 |
| 7 | 1 | 17 | 0.84 | 0.94 |
| 7 | 2 | 17 | 0.70 | 0.18 |
| 8 | 1 | 37 | 0.97 | 0.21 |
| 8 | 2 | 37 | 0.98 | 0.23 |
| 9 | 1 | 37 | 0.77 | 0.14 |
| 9 | 2 | 37 | 0.86 | 0.51 |
| | | Mean: | 0.80 | 0.35 |
| | | Mean (excluding 4, 2 and 5, 2): | 0.85 | 0.51 |

For 13/15 exogenous cardiac allografts, the endogenous and exogenous derivative curves had concordant sign for over 70% (mean=85±11%) of the given trial, indicating that the exogenous tissue was an effective relative endogenous rate sensor (Table 1).

In addition to their relative tracking ability, the majority (9/13) of exogenous hearts showed evidence of effective absolute sensing function (i.e., at any given time, the exogenous rate, appropriately scaled, could be used as an effective predictor of the natural heart rate). Exogenous-endogenous $\overline{RR}$ correlation computation was used to determine sensing function behavior. The correlation coefficient (defined for two N-length time series x and y as $$r = \frac{\sum_{i=1}^{N}(x_i - \overline{x})(y_i - \overline{y})}{\sqrt{\sum_{i=1}^{N}(x_i - \overline{x})^2 \cdot \sum_{i=1}^{N}(y_i - \overline{y})^2}},$$

where $\overline{x}$ is the mean of $\underline{x}$ was computed between each exogenous and corresponding endogenous $\overline{RR}$ time series.

Figure 3:
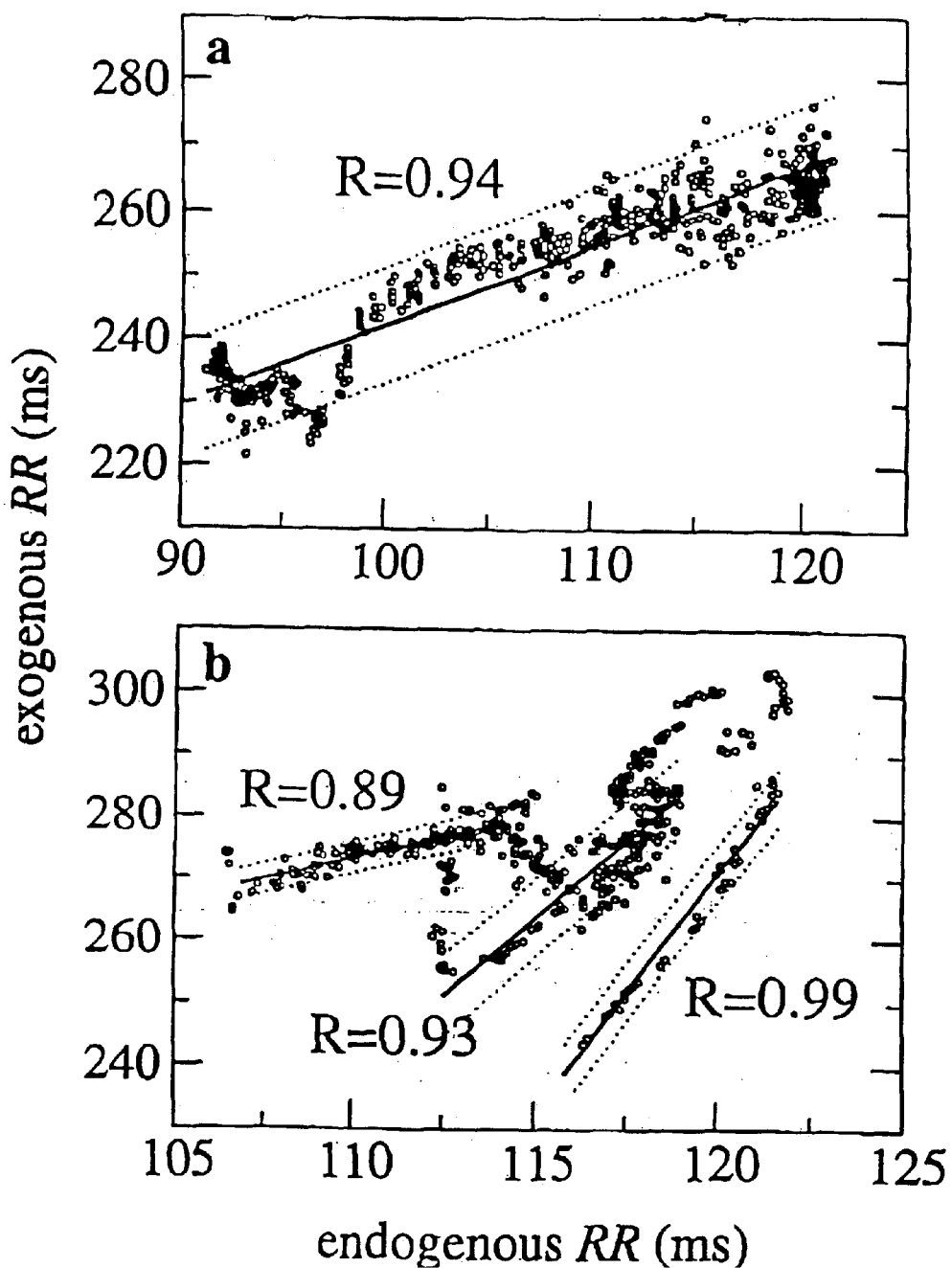
FIGS. 3a and 3b graphically depict exogenous RR versus endogenous RR for two separate mice (3a and 3b). The solid and dotted lines in each graph depict the linear regression fit and the 95% confidence interval of that fit, respectively.

Two types of absolute sensing function behavior were found: (i) a strong one-to-one linear relationship between the dynamics of the two hearts for the entire trial (in 5/9 exogenous hearts; e.g., FIG. 3a) or (ii) temporally-distinct highly correlated segments during the trial (in 4/9 exogenous hearts; e.g., FIG. 3b). Such temporal shifts in absolute sensing function indicate that the exogenous activity is mediated by a subset of the multiple inputs that govern the endogenous dynamics.

Figure 4:
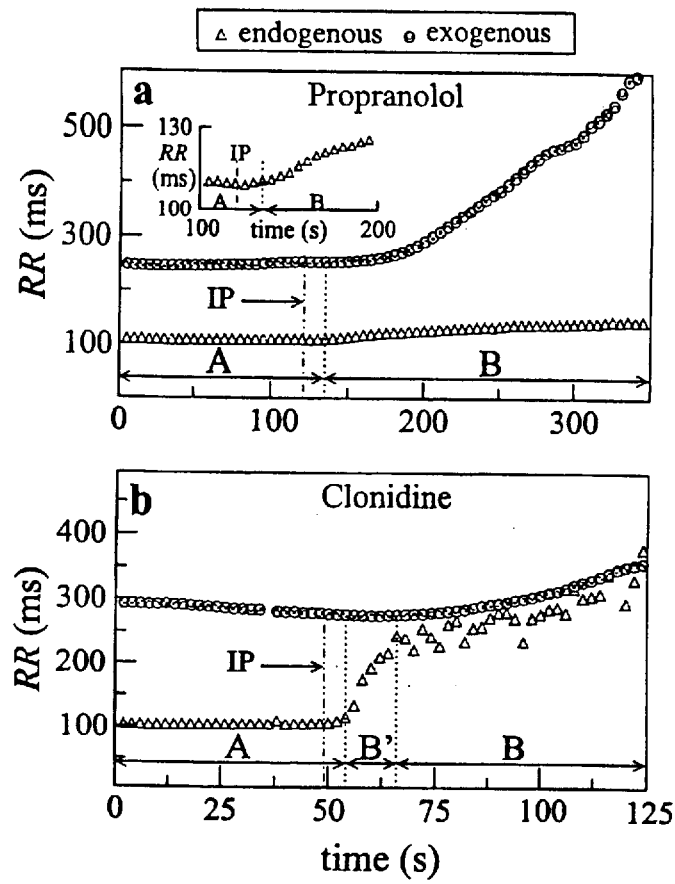
FIGS. 4a through 4c graphically depict endogenous and exogenous RR versus time for one mouse.

To identify the exogenous input subset, endogenous and exogenous chronotropic regulation by pharmacological manipulation were studied. A new set of mice, with pinnal hearts implanted as before, were subjected to pharmacological trials between 41 and 62 days post-transplantation. Separate experiments were performed with IP propranolol (100 μg) and IP clonidine (2.0 mg). To detect pharmacological rate effects, rate trends of distinct trial stages (as annotated in FIG. 4) were quantified by a normalized rate of change given by $m=((RR_f-RR_i)/RR)/t$, where $RR_i$ and $RR_f$ are the averages of the initial and final 3 RRs of a given stage, respectively, RR is the mean RR for the record, and t is the stage duration. Intraperitoneal propranolol was administered in an attempt to block humoral and autonomic β-adrenergic receptor pathways (FIG. 4a). As expected, shortly after injection, endogenous rate slowed. The exogenous rate underwent an even more dramatic decline, indicating that it is controlled by humoral and/or autonomic inputs.

To further define the nature of the exogenous inputs intraperitoneal clonidine trials were performed. In 6/7 trials, a rapid decrease in endogenous heart rate (lasting 10 to 30s), which is consistent with clonidine's reduction of efferent sympathetic nerve activity [34], was observed within 20s post-injection (FIG. 4b). In contrast, there was a negligible reduction in exogenous heart rate during this time, suggesting that the exogenous hearts are not under significant direct autonomic control. Following this initial post-injection stage, both hearts underwent a gradual heart-rate reduction consistent with a humoral response to clonidine's secondary effect of noradrenaline-release inhibition [35]. The results illustrated in FIG. 4 indicate that the chronotropic biosensing of the exogenous excitable tissue is mediated by predominately humoral influences.

The ability of 13/15 exogenous hearts to function as effective relative rate sensors, and to function as absolute rate sensors over all (e.g., FIG. 3a) or segments (e.g., FIG. 3b) of a trial is compelling evidence that exogenous excitable tissue can function as a responsive biosensor.

EXAMPLE II

Materials and Methods

Cardiac Transplant Model

Whole heart tissue-based in vivo biosensors were generated as previously described, employing neonatal (24 hr old) murine heart transplanted into the pinna of an isogeneic adult murine host (36, 37). Sets of mice were pretreated subcutaneously by pinneal injections of recombinant platelet derived growth factor (PDGF AB) (100 ng/20 μL PBS; R & D Research), vascular endogenous growth factor (VEGF) (100 ng/20 μL PBS; R & D Research) or vehicle alone, one day prior to receiving cardiac allograft transplants. The following day, a small pocket between the skin and cartilage was dissected toward the tip of the ear with delicate curved forceps. The total donor neonatal heart was excised without the pericardial sac and inserted into the ear pocket. Gentle pressure with the tips of the forceps was applied to the ear to express air from the pocket and facilitate the adherence between donor and recipient tissues. Two days after transplantation, the functional blood flow to the transplanted cardiac tissue was assessed by laser Doppler with an Advance Laser Flowmeter ALF21/21D (Advance, Tokyo) similar to that previously described (38). The PDGF AB dose response curve of chronotropic activity was also tested by pretreatment of the murine pinnae with a range of PDGF AB concentrations (1, 10 and 100 ng/20 μL PBS) or vehicle alone 1 day prior to receiving cardiac allograft transplants.

The ears were allowed to heal for 2 days prior to data acquisition and chronotropic activity within the first week post transplantation was measured as described below. N was ≧10 for each experimental set.

Embryonic Stem Cell-Derived Cardiac Myocyte Transplants

Cardiac cell-based based in vivo biosensors were generated with embryonic stem cell-derived cardiac myocytes in the place of whole neonatal cardiac tissue. Spontaneously beating cardiac myocytes were derived from E9 murine pluripotent embryonic stem cells (American Tissue Culture Company, Rockville, Md.) as previously described (39). Briefly, embryonic stem cells were cultivated on a feeder-layer of primary mouse embryonic fibroblasts in DMEM supplemented with non-essential amino acids, L-glutamine, 13-mercaptoethanol, 20% fetal calf serum, and 100 IU leukemia inhibiting factor (LIF). Droplets of cells ($10^4$ cells in 30 μL of culture media without LIF) were pipetted onto the lids of 3 cm bacteriological petri dishes filled with PBS and cultivated for two days. The resulting aggregates were transferred from the hanging drops into 6 cm dishes, were further cultivated for five days, and were then transferred to 12-well plates. Spontaneous chronotropic myocyte aggregates formed between 5 and 10 days after transfer and were subsequently employed in the murine pinnal transplant model in the place of the neonatal cardiac tissue. The mice were pretreated with PDGF (20 ng in 20 μL PBS, n=37; or vehicle alone, n=20) as described above. The following day, myocyte aggregates physically dissociated and suspensions of cells ($5\times10^4$ cells in 20 μL) were injected into the pinnal transplant pocket, which was then sealed via gentle pressure with forceps. The ears were allowed to heal for 2 days prior to data acquisition and chronotropic activity within the first week post transplantation was measured as described below.

Electrocardiograms

At various time times after transplantation, defined by the protocols described below, ECG activity of the endogenous and exogenous hearts were measured following anesthetization with avertin IP. ECGs were acquired for a minimum of 60 min via an A-M Systems Model 1700 four-channel differential AC amplifier. Signals were bandpass filtered between 3.0 and 100.0 Hz, notch-filtered at 60.0 Hz, amplified 1000X, and sampled at 500 Hz by a National Instruments AT-M.IO-1 6E-10 data acquisition board on a 266 MHz Intel Pentium-II computer running Real-Time Linux. Transplant activity was defined by two criteria. "Sustained" activity was characterized by consistent, monomorphic, periodic waveforms that continued for at least 200 seconds. "Sporadic" activity was characterized by a spectrum of activity including short-lived, irregular, multimorphic activity, regular activity lasting less than 200 seconds, and slow, scattered monomorphic waveforms that recurred multiple times throughout the recording period.

Quantitative Rate Analysis

Post-acquisition automatic (with manual correction as needed) ECG R-wave annotation was performed using custom Linux C++software (40). Mean RR intervals were computed every two seconds so dynamics of the endogenous and exogenous signals, which have different inherent rates, can be compared quantitatively at synchronized time slices.

Endogenous-Exogenous Cardiac Chronotropic Correlation

Recordings from the exogenous and endogenous tissue were analyzed for relative and absolute chronotropic correlation. Discrete data sets of at least 200 s were fit (using Matlab 5.3.1) to a continuous-time order polynomial function given by $RR(t) = a_0 t^P + a_1 t^{P-1} + \ldots a_p t + a_p$, with P selected as that order (P 25) for which: (i), RR(t), when evaluated at the same discrete-time slices as RR, accounts for at least 95% of the raw variability of RR (if this was not satisfied for any P<25, P was set to 25), and (ii) the exogenous and endogenous dRR(t)/dt functions, were computed analytically over the time course of the record, with interval time shift for exogenous lag, and demonstrated the highest concordance (i.e., the highest fraction of time that the two derivatives had the same sign). A concordance of>0.70 was employed as a measure of the ability of the exogenous heart to track the increases and decreases in endogenous rate. Absolute chronotropic correlation were measured by the coefficient (defined for N-length time series x and y as $r=[(x_i-x_{mean})(y_i-y_{mean})]/[(x_i-x_{mean})^2 (y_i-y_{mean})^2]$ computed between each exogenous and corresponding endogenous RR time series.

EXAMPLE III

Results

Enhanced Vascularization and Optimization of Tissue-Based Chronotropic Kinetics

Figure 5:
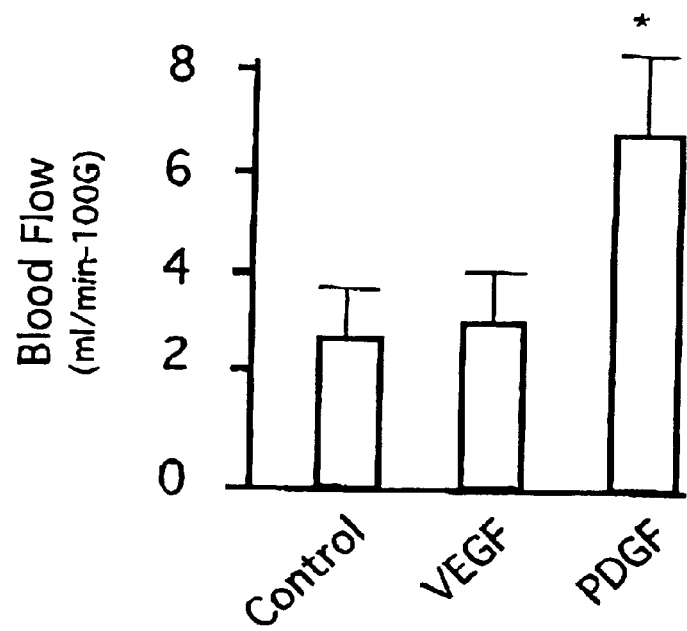
FIG. 5 graphically depicts PDGP AB Induction of Cardiac Allograft Rheology. Laser Doppler measured blood flow in the transplanted cardiac tissue after pinnal pretreatment with platelet-derived growth factor (PDGF) AB, vascular endothelial growth factor (VEGF) or vehicle alone.
p<0.05 vs control and VEGF pretreatments.

The potential of cytokine pretreatments to enhance the vascularization and chronotropic biosensing by the cardiac allografts that are regulated by blood-borne signals from the host was assessed. The host pinnae were injected with either vascular endothelial growth factor (VEGF), platelet-derived growth factor (PDGF) or vehicle alone and the following day were transplanted with neonatal cardiac allografts. Laser Doppler measurements revealed that the hearts transplanted into the pinnae pretreated with PDGF received over twice as much blood flow as those allograft implanted in the control and VEGF pretreated mice, FIG. 5.

Figure 6:
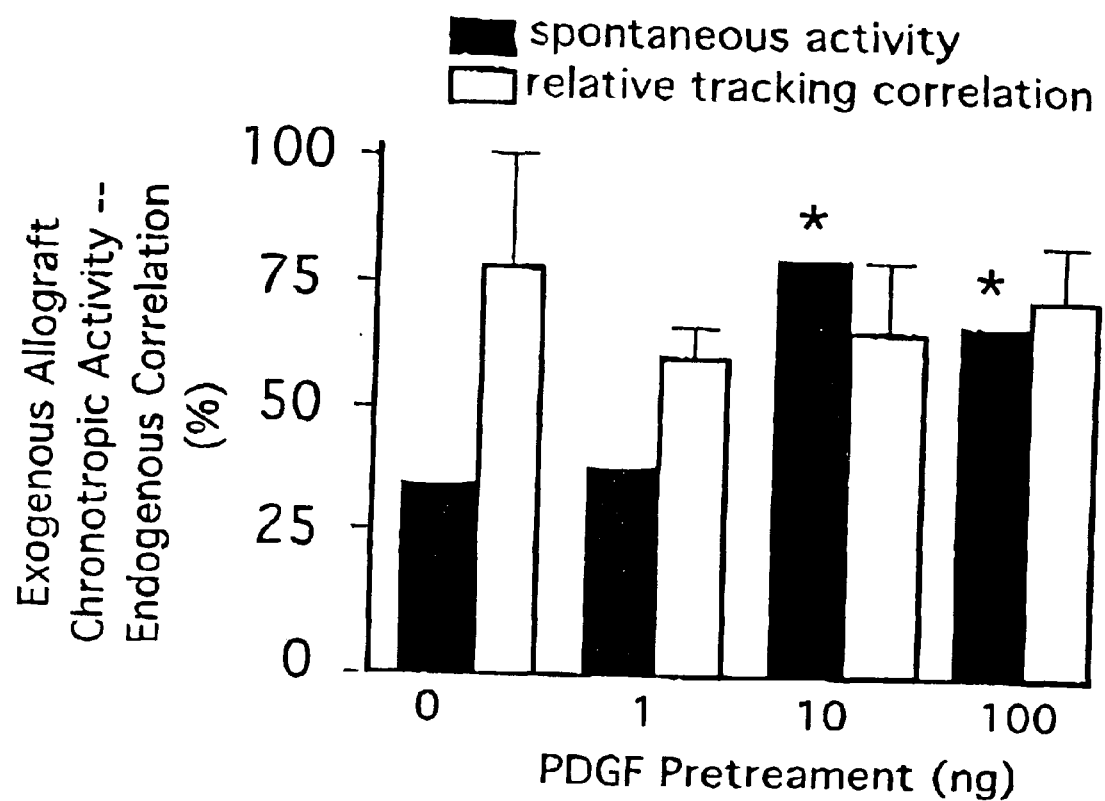
FIG. 6 graphically depicts PDGF Enhancement of Cardiac Tissue Chronotropic Activity. The Y axis measures the percentage of neonatal cardiac allografts demonstrating spontaneous electrocardiographic activity after pinnal pretreatment with PDGF (black bars). Relative tracking concordance of chronotropically competent allografts and endogenous electrocardiographic dynamics is shown by the open bars.
p<0.05 vs control and 1 ng pretreatments.

Based on the rheology results the role of PDGF pretreatment in the development of chronotropic activity in the transplanted hearts was evaluated. The mice were pretreated with a range of PDGF doses and spontaneous chronotropic activity of the cardiac allografts was recorded one week after transplantation. These studies revealed that almost twice as many exogenous hearts in the mice injected with 10 to 100 ng of PDGF had spontaneous chronotropic activity as compared to the control and 1 ng pretreatment groups, FIG. 6. In addition to measuring spontaneous beating, the ability of the transplanted cardiac tissue to emulate the chronotropic dynamics of the endogenous heart rate was also measured. These studies demonstrated similar average relative tracking concordance in all the transplants with spontaneous chronotropic activity regardless of the pretreatment groups, FIG. 6, indicating that the vascular threshold for the development of chronotropic activity is linked to biosensory potential of the intact cardiac tissue transplants.

Embryonic Stem Cell-Derived Cardiac Myocyte Biosensory Potential

Figure 7:
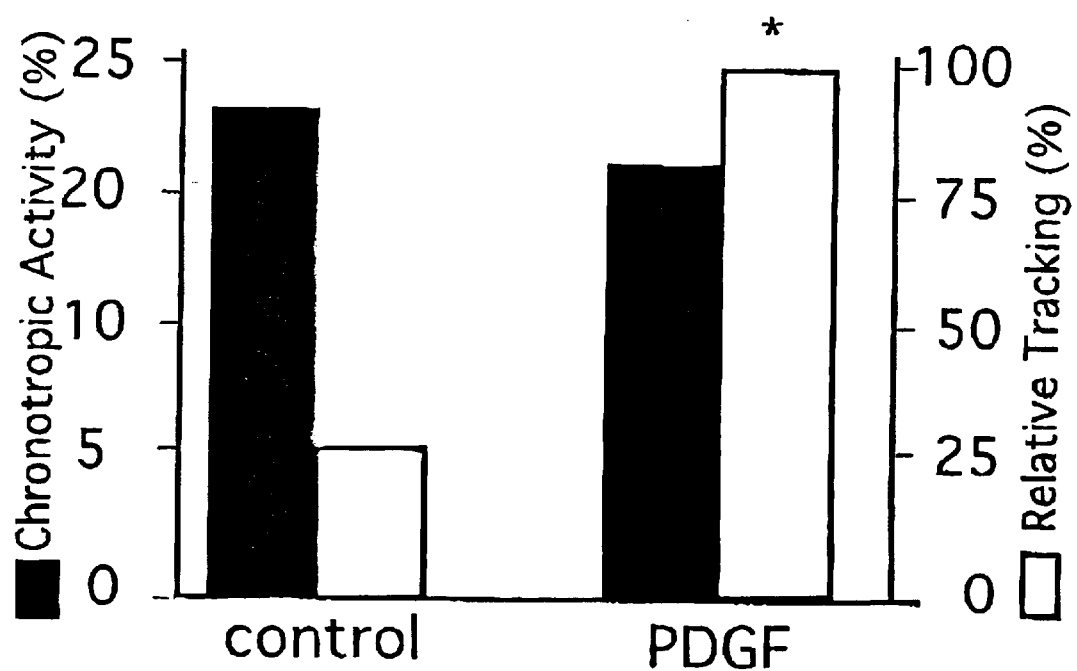
FIG. 7 graphically depicts PDGF Enhancement of Cardiac Myocyte-Based Chronotropic Activity and Biosensing. Transplanted embryonic stem cell-derived cardiac myocytes demonstrated sustained electropotential activity after pinnal pretreatment with PDGF or vehicle as a percentage of all allografts with electropotential activity as shown by the black bars. Percentage of transplanted cardiac myocyte spontaneous electropotential activity demonstrating concordant relative tracking (≧70%) is shown by open bars.
p<0.05 vs control and 1 ng pretreatments.

The defining of a set of host manipulations that enhance the kinetics of tissue-based chronotropic dynamics offered a foundation for developing the cell-based system to act as a biosensor of physiologic activity. To this end, embryonic stem cell-derived cardiac myocytes were generated and implanted into the murine pinna in the place of the neonatal cardiac tissue. Chronotropic dynamics recorded as described above for the cardiac allograft experiments. The majority of cellular transplants in both pretreatment groups demonstrated at least spontaneous or sustained electropotential activity (19/20 control transplants; 30/37 PDGF transplants). Moreover approximately a quarter of both of these electrically viable cellular transplants demonstrated sustained depolarizations, FIG. 7. Unlike the whole heart allografts however, pretreatment of the hosts with PDGF did not alter the development of chronotropic activity of the transplants, indicating that the myocytes received a sufficient vascular supply to maintain rhythmic electopotentials in the intact host.

Figure 8:
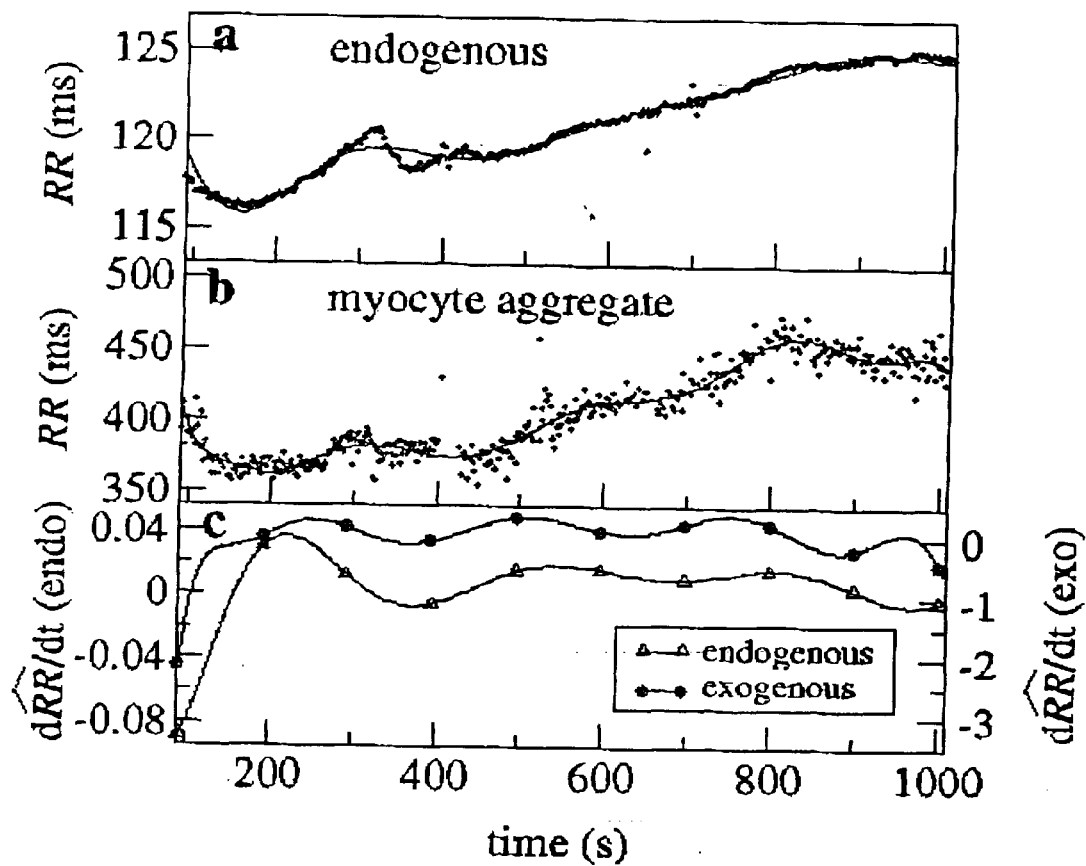
FIGS. 8a-8c show cardiac myocyte-based relative chronotropic biosensing activity measured by electrocardiographs.
Figure 9:
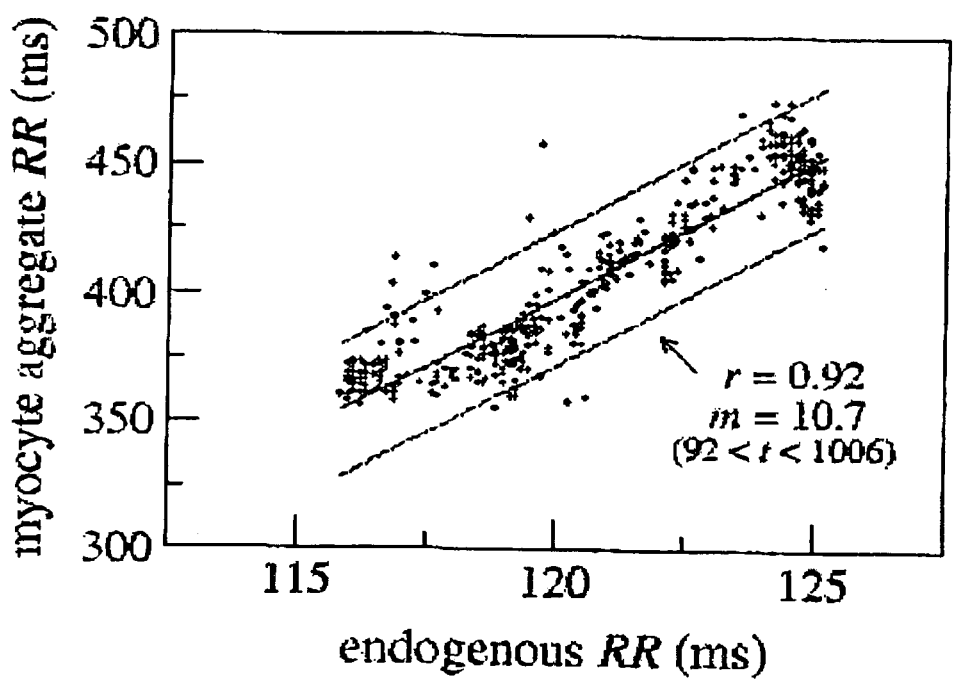
FIG. 9 is a representation of cardiac myocyte-based absolute chronotropic biosensing activity. Plotted is a representative example of ES-cardiac myocyte RR versus endogenous RR in a mouse pretreated with PDGF. The correlation coefficient r for the trial was .92.

The PDGF-mediated rheologic enhancement did improve the biosensory capacity of the transplanted cells. All of the sustained active cardiac myocytes transplanted into the pretreated pinnae acted as relative biosensors of the endogenous chronotropic dynamics, whereas only a quarter of the control transplants demonstrated relative biosensory potential, FIG. 8. Moreover, the PDGF pretreated group revealed a high degree of concordance of absolute tracking, FIG. 9 (myocyte RR vs endogenous RR r=0.80+/−0.15), indicating that signals from these cells could be employed as direct biosensors of the predicted endogenous heart rate These results demonstrate that a combination of enhanced angiogenic activity and embryonic cell-derived cardiac myocytes offer a biologically-based approach to predict physiologic chronotropic demands. Indeed, these findings extend the experimental results obtained in Example I where whole neonatal cardiac tissue was employed to detect the blood-borne signals that regulate the endogenous heart rate. The specific proangiogenic host interventions that increased the vascularization of the transplanted tissue markedly enhanced their development of chronotropic activity in the cardiac allografts. Moreover, this approach allowed the embryonic stem cell-derived cardiac myocytes to act as excellent relative and absolute biosensors of chronotropic dynamics. The present findings indicate that tissue-based biosensors may be used for the direct biologic integration of physiologic signals into electronic pacemaker technology in the clinical setting.

The interaction between the enhancement in transplant neovascularization and biosensory potential may be of increased importance in older individuals, who as a population have the highest prevalence of chronotropic incompetence. Previous studies have demonstrated that the angiogenic development of new blood vessels decreases with aging (41). Moreover, age-associated differences in cardiac angiogenesis correlate with a diminished capacity of cardiac microvascular endothelial cells to migrate into new capillary beds (42), and suggest that approaches that can restore this angiogenic activity may be critical in the translation of biologically-based biosensor approaches to improve chronotropic treatments.

References

1. Brignole, M., C. Menozzi, G. Lolli, D. Oddone, L. Gianfranchi, and A. Bertulla. 1990. Pacing for carotid sinus syndrome and sick sinus syndrome. *Pacing C/in Electrophysiol.* 13:2071–2075.
2. Ogawa, H., T. Inoue, S. Miwa, T. Fujimoto, Y Ohnishi, and Ii. Fukuzaki. 199L Heart rate responses to autonomic drugs in sick sinus syndrome—correlation with syncope and electrophysiologic data. Jpn *Circ* .1. 55:15–21.
3. Rodriguez, R. D., and D. D. Schocken. 1990. Update on sick Sinus syndrome, a cardiac disorder of aging. *Geriatrics.* 45:26–30, 33–26.
4. Windecker, 5., R. S. Bubien, L. Halperin, A. Moore, and O. K. Kay. 1998. Two-year experience with rate-modulated pacing controlled by mixed venous oxygen saturation. *Pacing Clin Electrophysiol.* 21:1396–1404.
5. Clementy, I, S,S. Barold, S. Garrigue, D. C. Shah, P. Jais, P. Le Metayer, and M. Haissaguerre. 1999. Clinical significance of multiple sensor options: rate response optimization, sensor blending, and Wending. *Am J Cardiol.* 83:166D-171D.
6. Greco, E.1v1$_7$ S. Guardini, M. Ferrario, and S. Romano. 2000. How to program rate responsive pacemakers. *Pacing C/in Electrophysiol.* 23:165–173.

7. Celiker, A., N. Ceviz, D. Alehan, M. K. Lenk, and S. Ozme. 1998. Comparison of normal sinus rhythm and pacing rate in children with minute ventilation single chamber rate adaptive permanent pacemakers *Pacing Clin Electrophysiol* 21:2100–2104.
8. Moura, P. L, L. J. Gessaman, T. Lai, J. D. Gallagher, M. White, and D. P. Morse. 1987 Chronotropic response of an activity detecting pacemaker compared with the normal sinus node. *Pacing Clin E/ectrophysiol.* 10:78–86.
9. Lau, C. R., Y. T. Tai, P.C. Fong, G. E. Cheng, and F. L. Chung. 1990. Pacemaker mediated tachycardias in single chamber rate responsive pacing. *Pacing Clin Electrophysiol* 13:1575–1579.
10. Strobel, I. S., and G. N. Kay. 2000. Programming of sensor driven pacemakers. *Cardiol Clin.* 18)157–176, ix.
11. Sugiura, T. N. Sugiura, T. Kazui, and Y. Harada. 1998. A self-tuning effect of membership functions in a fuzzy-logic-based cardiac pacing system. *J Med Eng Technol* 22:137–143.
12. Leung, S. K., C. P. Lau, M. O. Tang, Z. Leung, and K. Yakimow. 1998. An integrated dual sensor system automatically optimized by target rate histogram *Pacing Clin Electrophysiol.* 21:1559–1566.
13. Clementy, J. 1998. Dual chamber rate responsive pacing system driven by contractility: final assessment alter 1-year follow-up. The European PEA Clinical Investigation Group. *Pacing Clin Electrophysiol.* 21:2192–2197.
14. Boute, W., U. Gebbardt, and M. J. Begemann. 1988. Introduction of an automatic QT interval driven rate responsive pacemaker. *Pacing Clin Electrophysiol.* 11:1804–1814.
15. den Heijer, P., D. Nagelkerke, E. J. Perrins, B. Horstmann, R. J. Van Woersem, W. Niederlag, L. Jordaens, P. De Wilde, A. J. Hameleers, W. Bout; and et al. 1989. Improved rate responsive algorithm in QT driven pacemakers—evaluation of initial response to exercise. Pacing C/in Electrophysiol. 12:805–811.
16. Connelly, D. T. 1993. Initial experience with a new single chamber, dual sensor rate responsive pacemaker. The Topaz Study Group. *Pacing C/in Electrophysiol.* 16:1833–1841.
17. Andersson, J. L., S. E. Hedberg, J. Hirschberg, and H. Schuller. 1998. A software sensor using neural networks for detection of patient workload. *Pacing Chin Electrophysiol.* 21:2204–2208.
18. Wang, Ti., W. J. Chen, C. S Liau, and Y. T. Lee. 1994. Sick Sinus syndrome as the early manifestation of cardiac hemochromatosis. *J Electrocardiol.* 27:91–96.
19. Sutton, R., and R. A. Kenny. 1986. The natural history of sick sinus syndrome. *Pacing C/in Electrophysiol* 9:1110–1114.
20. J. J. Pancrazio, J. P. Whelan, D. A. Borkholder, W. Ma, D. A. Stenger. *Annals of Biomedical Engineering* 27, 697 (1999).
21. C. J. Cook. *Nature Biotechnology* 15, 467 (1997).
22. C. A. Rowe-Taitt, et al. *Biosensors & Bioelectronics* 14, 785 (2000).
23. P. Mulchandani, A. Mulchandani, I. Kaneva, W. Chen. *Biosensors & Bioelectronics* 14, 77 (1999).
24. S. J. Updike, M. C. Shults, B. J. Gilligan, R. K. Rhodes. *Diabetes Care* 23, 208 (2000).
25. B. A. Cornell, et al. *Nature* 387, 580 (1997).
26. L. Q. Luo, X. R. Yang, B. K. Wang. *Analytical Letters* 32,1271 (1999).
27. A. Marshall, J. Hodgson. *Nature Biotechnology* 16, 27 (1998).
28. J. Fritz, et al. *Science* 288, 316 (2000).
29. J. C. Owicki, J. W. Parce. *Biosensors & Bioelectronics* 7, 255 (1992).
30. L. Bousse. *Sensors and Actuators B-Chemical* 34, 270 (1996).
31. M. Naessens, C. Tran-Minh. *Biosensors & Bioelectronics* 13, 341 (1998).
32. R. I. Fulmer, A. T. Cramer, R. A. Liebelt, A. G. Liebelt. *American Journal of Anatomy* 113, 273 (1963).
33. J. M. Edelberg, W. C. Aird, R. D. Rosenberg. *Journal of Clinical Investigation* 101, 337 (1998).
34. K. K. Wong. *Artery* 20, 180 (1993).
35. F. Anglade, et al. *British Journal of Pharmacology* 91, 481 (1987).
36. Aird, W. C., J. M. Edelberg, II. Weiler-Guettler, W. W. Simmons, T. W Smith and R. D Rosenberg. 1997. Vascular bed-specific expression of an endothelial cell gene is programmed by the tissue microenvironment. .1 *Ce/i J3ioL* 138:1117–1124.
37. Edelberg, J. M., W. C. Aird, and R. D. Rosenberg. 1998. Enhancement of murine cardiac chronotropy by the molecular transfer of the human beta2 adrenergic receptor cDNA. *JC/in Invest.* 101:337–343.
38. Rendell, M. S., MY>Finnegan, IC. Healy, A. Lind, B. K. Milliken, D. E. Finney, and R. F. Bonner. 1998. The relationship of laser-Doppler skin blood flow measurements to the cutaneous microvascular anatomy. *Microvasc Res.* 55:3–13.
39. Maltsev, V. A., J. Rohwedel, J. Hescheler, and A. M. Wobus. 1993. Embryonic stem cells differentiate in vitro into cardiomyocytes representing sinusnodal, a trial and ventricular cell types. Mech Dev. 44:41–50.
40. Christini, 0.1., K. M. Stein, S. M. Markowitz, and B. B. Lerman 1999. Practical real-time computing system for biomedical experiment interface. Ann Biomed Eng. 27:180–186.
41. Rivard, A., Y E. Fabre, M. Silver, D. Chen, T. Murohara, M. Kearney, M Magner, I. Asahara, and J. M. Isner. 1999. Age-dependent impairment of angiogenesis. Circulation. 99:111–120.
42. Anversa, P., J. M. Capasso, R. Ricci, E. H. Sonnenblick, and G. Olivetti. 1989. Morphometric analysis of coronary capillaries during physiologic myocardial growth and induced cardiac hypertrophy: a review. Int J Microcirc Clin Exp. 8:353–363.
43. Makino, S., K. Fukuda, S. Miyoshi, F. Konishi, H. Kodama, J Pan, M. Sano, T. Takahashi, S. Hori, H. Abe, .1 Hata, K Umezawa, and S. Ogawa. 1999. Cardiomyocytes can be generated from marrow stromal cells in vitro. J Clin Invest 103:697–705.

What is claimed is:

1. An implantable physiological or pathophysiological biosensor comprising: tissue or cells capable of carrying out a physiological or pathophysiological function, wherein the tissue or cells can be coupled via an electrical interface to an electronic measuring device or an electronic amplifying device, and wherein the biosensor monitors a chemical, physiological or pathophysiological variable associated with an endogenous physiological or pathophysiological function in a mammalian subject.

2. An implantable physiological or pathophysiological biosensor comprising: tissue or cells capable of carrying out a physiological or pathophysiological function, wherein the tissue or cells can be coupled via an electrical interface to endogenous tissue or cells, and wherein the biosensor may be used to monitor a chemical, physiological or pathophysiological variable associated with an endogenous physiological or pathophysiological function in a mammalian subject.

3. The biosensor according to claim 1 or 2, wherein the tissue or cells are excitable tissue or cells.

4. The biosensor according to claim 3, wherein the excitable tissue or cells are cardiac tissue or cells.

5. The biosensor according to claim 3, wherein the tissue or cells are neuronal tissue or cells.

6. The biosensor according to claim 1 or 2, wherein the tissue or cells are molecularly, genetically, or cellularly engineered.

7. The biosensor according to claim 1 or 2, wherein the physiological or pathophysiological variable is heart rate regulation or heart rate dynamics.

8. The biosensor according to claim 1 or 2, wherein the physiological or pathophysiological variable is a level or activity of at least one of blood glucose, insulin, thyroid hormone, clotting factors or components, endocrine hormone, paracrine hormone, autocrine hormone, antibodies, receptor antagonists, ligands, antigens, antagonists, signal pathway cofactors, signal pathway components, pathogens, drugs, metabolites, or toxins.

9. The biosensor according to claim 1 or 2, wherein the biosensor is implanted or inserted in an animal.

10. The biosensor according to claim 9 wherein the animal is a mammal.

11. The biosensor according to claim 10, wherein the mammal is selected from the group consisting of a mouse, rat, rabbit, pig, cat, dog, cattle, horse, and sheep.

12. The biosensor according to claim 10, wherein the mammal is a human.

13. The biosensor according to claim 1 or claim 2 wherein the tissue or cells are incorporated within a device.

14. The biosensor of claim 13 wherein the device is at least one of a tube, tubing, catheter, wire, wire leads, or an electronic pacemaker.

15. A method for monitoring a physiological or pathophysiological function of a subject, said method comprising: placing into a site within a subject isolated tissue or cells wherein the site can be distant from an endogenous site of the physiological or pathophysiological function within the subject, and wherein the tissue or cells may be used to monitor a chemical, physiological or pathophysiological variable associated with the endogenous site of the physiological or pathophysiological function of the subject, and; monitoring the physiological or pathophysiological function of the exogenous tissue or cells placed therein.

16. The method according to claim 15, wherein the tissue or cells are excitable tissue or cells.

17. The method according to claim 16 wherein the excitable tissue or cells are cardiac tissue or cells.

18. The method according to claim 16, wherein the excitable tissue or cells are neuronal tissue or cells.

19. The method according to claim 15, wherein the tissue or cells are coupled via an electrical interface to endogenous tissue or cells.

20. The method according to claim 15, wherein the tissue or cells are coupled via an electrical interface to an electronic measuring device or an electric amplifying device.

21. The method according to claim 15, wherein the tissue or cells are molecularly, genetically, or cellularly engineered.

22. The method according to claim 15, wherein the physiological or pathophysiological variable is heart rate regulation or heart rate dynamics.

23. The method according to claim 15, wherein the chemical, physiological or pathophysiological variable is a level or activity of at least one of blood glucose, insulin, thyroid hormone, clotting factors and components, endocrine hormone, paracrine hormone, autocrine hormone, antibodies, receptor antagonists, ligands, antigens, antagonists, signal pathway cofactors, signal pathway components, pathogens, drugs, metabolites, or toxins.

24. The method according to claim 15, wherein the tissue or cells can be incorporated into a device that is placed inside an animal.

25. The method of claim 24 wherein the device is at least one of a tube, tubing, catheter, wire, wire leads, or an electronic pacemaker.

26. The method according to claim 24, wherein the animal is a mammal.

27. The method according to claim 26, wherein the mammal is selected from the group consisting of a mouse, rat, rabbit, pig, cat, dog, cattle, horse, and sheep.

28. The method according to claim 26, wherein the mammal is a human.

29. A method of regulating output of a signal, substance, or action in a subject, said method comprising: placing within the subject, exogenous tissue or cells capable of carrying out a physiological or pathophysiological function, wherein the exogenous tissue or cells can be used to monitor a chemical, physiological or pathophysiological variable associated with the physiological or pathophysiological function; coupling the exogenous tissue or cells to an interventional device or a delivery device; and regulating the output of a signal, substance, or action from the interventional device or delivery device in response to the physiological or pathophysiological function of the exogenous tissue or cells.

30. The method according to claim 29, wherein the signal is an electrical signal.

31. The method according to claim 29, wherein the signal is a chemical signal.

32. The method according to claim 29, wherein the tissue or cells are excitable tissue or cells.

33. The method according to claim 32, wherein the excitable tissue or cells are cardiac tissue or cells.

34. The method according to claim 32, wherein the excitable tissue or cells are neuronal tissue or cells.

35. The method according to claim 29, wherein the tissue or cells are molecularly, genetically, or cellularly engineered.

36. The method according to claim 29, wherein the physiological or pathophysiological variable is heart rate regulation or heart rate dynamics.

37. The method according to claim 29, wherein the chemical, physiological or pathophysiological variable is a level or activity of at least one of blood glucose, insulin, thyroid hormone, clotting factors and components, endocrine hormone, paracrine hormone, autocrine hormone, antibodies, receptor antagonists, ligands, antigens, antagonists, signal pathway cofactors, signal pathway components, pathogens, drugs, metabolites or toxins.

38. The method according to claim 29, wherein the tissue or cells are implanted in a mammal.

39. The method according to claim 29, wherein the tissue or cells are incorporated into a device that is placed inside the subject.

40. The method of claim 39 wherein the device is at least one of a tube, tubing, catheter, wire, wire leads, or an electronic pacemaker.

41. The method according to claim 38, wherein the mammal is selected from the group consisting of a mouse, rat, rabbit, pig, cat, dog, cattle, horse, and sheep.

42. The method according to claim 38, wherein the mammal is a human.

43. The method according to claim 29, wherein the delivery device delivers a drug or compound.

44. The method according to claim 29 wherein the interventional device is an alarm system or mechanical device.

45. The method according to claim 29 wherein the delivery device is a an electronic pacemaker, insulin pump, or drug pump.

46. The method according to claim 29, wherein the delivery device delivers electrical stimuli or mechanical stimuli.

47. A system for controlling heart function comprising: exogenous tissue or cells that can be placed within a subject; and an electrical connection that can be placed between the exogenous tissue or cells and a natural pacemaker region of the subject's heart, wherein the exogenous tissue or cells are capable of carrying out a physiological or pathophysiological function and may be used to monitor a chemical, physiological or pathophysiological variable associated with a physiological or pathophysiological function of the subject's heart.

48. The system according to claim 47 further comprising: an amplifier to boost the signal from the exogenous tissue or cells.

49. The system according to claim 47 wherein the exogenous tissue is connected to an electronic pacemaker.

50. The system according to claim 47 wherein the exogenous tissue comprises cells which are molecularly, genetically, or cellularly engineered.

51. The system according to claim 47 wherein the exogenous tissue or cells are incorporated into a device that i-scan be placed inside the subject.

52. The system of claim 51 wherein the device is at least one of a tube, tubing, catheter, wire, or wire leads.

53. The system according to claim 47 wherein the exogenous tissue or cells are cardiac or neuronal tissue or cells.

54. The biosensor according to claim 1 or 2, wherein the tissue or cells receive blood-borne signals from the mammalian subject.

55. An implantable physiological or pathophysiological biosensor comprising genetically modified cells that can be coupled via an electrical interface to an electronic measuring device or an electronic amplifying device, wherein the genetically modified cells can be implanted into a mammalian subject at a site distant from a natural site for a physiological or pathophysiological function of the subject, and wherein the genetically modified cells monitor a chemical, physiological or pathophysiological variable associated with the physiological or pathophysiological function of the subject.

56. An implantable physiological or pathophysiological biosensor comprising: genetically modified cells that can be coupled via an electrical interface to endogenous tissue or cells, wherein the genetically engineered cells can be implanted into a mammalian subject at a site distant from a natural site for a physiological or pathophysiological function of the subject, and wherein the genetically modified cells monitor or modulate a chemical, physiological or pathophysiological variable associated with the physiological or pathophysiological function of the subject.

57. An implantable physiological or pathophysiological biosensor comprising in vitro or ex vivo modified stem cells that can be coupled via an electrical interface to an electronic measuring device or an electronic amplifying device, wherein the in vitro or ex vivo modified stem cells can be implanted into a mammalian subject at a site distant from a natural site for a physiological or pathophysiological function of the subject, and wherein the in vitro or ex vivo modified stem cells monitor a chemical, physiological or pathophysiological variable associated with the physiological or pathophysiological function of the subject.

58. An implantable physiological or pathophysiological biosensor comprising: in vitro or ex vivo modified stem cells that can be coupled via an electrical interface to endogenous tissue or cells, wherein the in vitro or ex vivo modified stem cells can be implanted into a mammalian subject at a site distant from a natural site for a physiological or pathophysiological function of the subject, and wherein the in vitro or ex vivo modified stem cells monitor or modulate a chemical, physiological or pathophysiological variable associated with the physiological or pathophysiological function of the subject.

* * * * *

UNITED STATES PATENT AND TRADEMARK OFFICE
CERTIFICATE OF CORRECTION

| | | |
|---|---|---|
| PATENT NO. | : 6,650,919 B2 | Page 1 of 1 |
| APPLICATION NO. | : 09/848064 | |
| DATED | : November 18, 2003 | |
| INVENTOR(S) | : Edelberg et al. | |

It is certified that error appears in the above-identified patent and that said Letters Patent is hereby corrected as shown below:

In column 1, lines 7-9, delete "This invention was made with government support under National Institutes of Health, Grant No. PO 1 HL593 12. The Government may have certain rights in the invention." and insert -- This invention was made with government support under Grant No. PO1 HL59312 awarded by National Institutes of Health. The government has certain rights in the invention. --, therefor.

Signed and Sealed this

Fourth Day of November, 2008

JON W. DUDAS
*Director of the United States Patent and Trademark Office*